(12) United States Patent
Takahashi

(10) Patent No.: US 9,540,672 B2
(45) Date of Patent: Jan. 10, 2017

(54) METHOD OF PRODUCING GLYCOLIPIDS

(71) Applicant: Kao Corporation, Chuo-ku, Tokyo (JP)

(72) Inventor: Fumikazu Takahashi, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 14/430,752

(22) PCT Filed: Oct. 3, 2013

(86) PCT No.: PCT/JP2013/076958
§ 371 (c)(1),
(2) Date: Mar. 24, 2015

(87) PCT Pub. No.: WO2014/061459
PCT Pub. Date: Apr. 24, 2014

(65) Prior Publication Data
US 2015/0267235 A1 Sep. 24, 2015

(30) Foreign Application Priority Data
Oct. 18, 2012 (JP) ................. 2012-230994

(51) Int. Cl.
*C12P 19/44* (2006.01)
*C12N 1/15* (2006.01)
*C12N 9/04* (2006.01)
*C12N 15/09* (2006.01)
*C12N 15/81* (2006.01)
*C12P 7/64* (2006.01)

(52) U.S. Cl.
CPC ............ *C12P 19/44* (2013.01); *C12N 9/0006* (2013.01); *C12N 15/09* (2013.01); *C12N 15/815* (2013.01); *C12P 7/64* (2013.01); *C12Y 101/03013* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 6,433,152 B1 | 8/2002 | Lang et al. | |
| 7,160,708 B2 * | 1/2007 | Eirich .................. | C12N 9/0006 435/18 |
| 2011/0136110 A1 * | 6/2011 | Van Bogaert .......... | C12N 15/01 435/6.1 |
| 2013/0035403 A1 | 2/2013 | Schaffer et al. | |

FOREIGN PATENT DOCUMENTS

| | | |
|---|---|---|
| JP | 2001-522597 A | 11/2001 |
| WO | WO 2009/141407 A2 | 11/2009 |
| WO | WO 2011/008231 A2 | 1/2011 |
| WO | WO 2011/008232 A2 | 1/2011 |
| WO | WO 2011/061032 A2 | 5/2011 |
| WO | WO 2012/080116 A1 | 6/2012 |

OTHER PUBLICATIONS

Fleurackers et al., On the production and identification of medium-chained sophorolipids, Eur. J. Lipid Sci. Technol., 2010, 112, 655-62.*
Van Bogaert et al., Microbial synthesis of sophorolipids, Process Biochem., 2011, 46, 821-33.*
Domon et al., Mass spectrometery and protein analysis, Science, 2006, 312, 212-17.*
Van Bogaert et al., Knocking out the MFE-2 gene of Candida bombicola leads to improved medium-chain sophorolipid production, FEMS Yeast Res., 2009, 9, 610-17.*
GenBank, Accession No. AB907775.1, 2014, www.ncbi.nlm.nih.gov.*
Uniprot, Accession No. G8BG15, 2012, www.uniprot.org.*
Compton, Degenerate primers for DNA amplification, PCR Protocols, Chapter 5, 1990, 39-45.*
International Search Report (ISR) for PCT/JP2013/076958; I.A. fd: Oct. 3, 2013, mailed Nov. 5, 2013, the Japanese Patent Office, Tokyo, Japan.
International Preliminary Report on Patentability (IPRP) including the Written Opinion of the International Searching Authority (PCT Rule 44*bis*) for PCT/JP2013/076958; I.A. fd: Oct. 3, 2013, issued Apr. 21, 2015, by the International Bureau of WIPO, Geneva, Switzerland.
Hommel, R et al., "Evidence for two fatty alcohol oxidases in the biosurfactant-producing yeast *Candida* (*Torulopsis*) *bombicola*," FEMS Microbiol Lett, Jul. 1990; 70: 183-186, Oxford University Press, Oxford, UK.
Hommel, RK at al., "The inducible microsomal fatty alcohol oxidase of *Candida* (*Torulopsis*) *apicola*," Appl Microbiol Biotechnol, 1994; 40: 729-734, Springer International, New York, NY.
Kemp, GD et al., "Occurrence of fatty alcohol oxidase in alkane- and fatty-acid-utilising yeasts and moulds," Appl Microbiol Biotechnol, 1994; 40: 873-875, Springer International, New York, NY.
Vanhanen, S et al., "A Consensus Sequence for Long-chain Fatty-acid Alcohol Oxidases from *Candida* Identifies a Family of Genes Involved in Lipid ω-Oxidation in Yeast with Homologues in Plants and Bacteria," J. Biol. Chem., Feb. 2000; 275: 4445-4452, American Society for Biochemistry and Molecular Biology, Baltimore, MD.

(Continued)

*Primary Examiner* — Robert Mondesi
*Assistant Examiner* — Todd M Epstein
(74) *Attorney, Agent, or Firm* — Sterne, Kessler, Goldstein & Fox P.L.L.C.

(57) ABSTRACT

A protein selected from the following (a) to (c), a gene encoding the protein, a transformant in which the gene is subjected to deletion, mutation or repression of gene expression, and a method of producing a glycolipid using the transformant are provided, wherein: (a) is a protein consisting of an amino acid sequence set forth in SEQ ID NO: 1; (b) is a protein consisting of an amino acid sequence having 50% or more identity with the amino acid sequence set forth in SEQ ID NO: 1, and having alcohol oxidase activity; and (c) is a protein consisting of an amino acid sequence in which one to several amino acids are subjected to deletion, substitution, insertion or addition in the amino acid sequence set forth in SEQ ID NO: 1, and having alcohol oxidase activity.

18 Claims, 4 Drawing Sheets

(56) References Cited

OTHER PUBLICATIONS

Saerens, KM at al., "One-step production of unacetylated sophorolipids by an acetyltransferase negative *Candida bombicola*," Biotechnol Bioeng, Dec. 2011; 108(12): 2923-2931, Wiley, Hoboken, NJ.

Van Bogaert, Ina et al., "The biosynthetic gene cluster for sophorolipids: a biotechnological interesting biosurfactant produced by *Starmerella bombicola*," Molecular Microbiology, (2013: first published online Mar. 21, 2013), 88(3): 501-509, Blackwell Scientific Publications, Oxford, MA.

Brakemeier, A et al., "Microbial alkyl-sophorosides based on 1-dodecanol or 2-, 3- or 4-dodecanones," Biotechnology Letters, Mar. 1998, 20(1): 215-218, Kluwer Academic Publishers, Dordrecht, Netherlands.

Extended European search report, including the supplementary European search report and the European search opinion, for EP Application No. 13846434.2, dated May 24, 2016, European Patent Office, Munich, Germany.

Database UNIPROT [Online], retrieved from EBI accession No. UNIPROT:Q9P8D9, Oct. 1, 2000, sequence version 1, entry version 65, RecName: Full=Long-chain-alcohol oxidase {ECO:0000256 | PIRNR028937}; EC=1.1.3.20 {ECO:0000256 | PIRNR028937} downloaded May 12, 2016.

\* cited by examiner

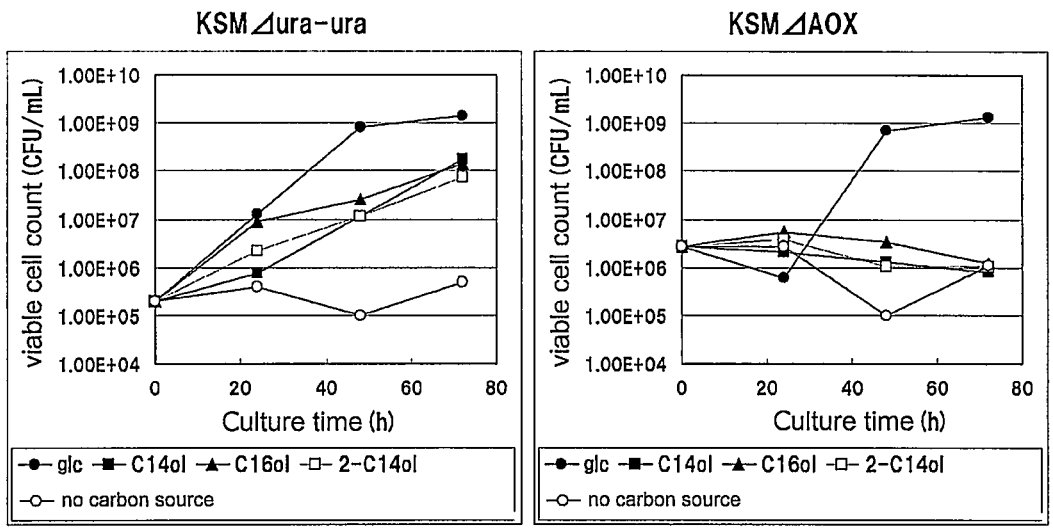

METHOD OF PRODUCING GLYCOLIPIDS

TECHNICAL FIELD

The present invention relates to a novel alcohol oxidase, and a gene encoding the same. Further, the present invention relates to a transformant in which the gene is subjected to deletion or the like, and a method of producing glycolipids using the transformant.

BACKGROUND ART

An alkyl glycoside and a sophorose lipid are glycolipids and are formulated with various kinds of detergents as a surfactant.

Industrial production of the alkyl glycoside or the sophorose lipid is mainly made by chemical synthesis using sugar and alcohol as raw materials, but has problems of needing a large amount of raw material alcohol and causing denaturation of raw material glucose because a reaction under a high temperature and a high pressure is carried out.

From such situations, technologies of producing glycolipids using microorganisms have been studied in pursuit of high production efficiency. For example, it has been reported that when *Candida bombicola*, one of yeast, is cultured in a medium containing sugar and alcohol, alkyl sophorosides or sophorose lipids are obtained as a product (Patent Literature 1 and Non-Patent Literature 1).

CITATION LIST

Patent Literatures

Patent Literature 1: U.S. Pat. No. 6,433,152

Non-Patent Literatures

Non-Patent Literature 1: Biotechnology Letters, Volume 20, No. 3, 1998, pp. 215-218

SUMMARY OF INVENTION

The above production method using a microorganism allows production of glycolipids under ordinary temperature and normal pressure, but has a problem of a significantly low yield of the glycolipids based on raw material alcohol.

Accordingly, the present invention is contemplated for providing a microorganism transformant that can produce glycolipids with satisfactory productivity under ordinary temperature and normal pressure, and a method for producing glycolipids using the transformant.

The present inventors made extensive studies on technologies on producing glycolipids using microorganisms. As a result, they found that a new alcohol oxidase is involved in an alcohol metabolic pathway of *Candida bombicola*. Further, the present inventors also found that productivity of glycolipids is significantly improved with a transformant in which a function of this alcohol oxidase gene decreases. The present invention was completed based on these findings.

The present invention relates to a transformant, wherein, in a host having a gene encoding any one of the following proteins (a) to (c), the gene is subjected to deletion, mutation or repression of gene expression, and alcohol oxidase activity decreases in comparison with the host:
(a) A protein consisting of an amino acid sequence set forth in SEQ ID NO: 1;
(b) A protein consisting of an amino acid sequence having 50% or more identity with the amino acid sequence set forth in SEQ ID NO: 1, and having alcohol oxidase activity; and
(c) A protein consisting of an amino acid sequence in which one to several amino acids are subjected to deletion, substitution, insertion or addition in the amino acid sequence set forth in SEQ ID NO: 1, and having alcohol oxidase activity.
(Hereinafter, referred to as "the transformant of the present invention")

The present invention also relates to a method of producing a glycolipid, comprising the following steps (1) and (2):
(1) A step of culturing the above transformant in a medium containing alcohol and sugar; and
(2) A step of collecting a glycolipid from the resulting cultured product.
(Hereinafter, referred to as "the method of producing a glycolipid of the present invention")

The present invention also relates to a gene encoding any one of the above proteins (a) to (c).
(Hereinafter, referred to as "the gene of the present invention")

The present invention also relates to a protein selected from the above (a) to (c).
(Hereinafter, referred to as "the protein of the present invention")

The present invention provides a new alcohol oxidase useful for efficient production of glycolipids, and a gene encoding the same. The present invention also provides a transformant that is excellent in production ability of glycolipids. The present invention further provides a method for producing glycolipids, being excellent in productivity and useful for industrial production of the glycolipids.

Other and further features and advantages of the invention will appear more fully from the following description, taken in connection with the accompanying drawings.

BRIEF DESCRIPTION OF DRAWINGS

FIG. 1 is a diagram showing a comparison of partial sequences of an ura3 gene in a KSM36 strain, an NBRC10243 strain and a KSMΔura3 strain prepared in Examples.

FIG. 2 is a diagram showing time courses of viable cell counts when a KSMΔura-ura strain and a KSMΔAOX strain prepared in Examples are cultured in each medium containing a different carbon source.

MODE FOR CARRYING OUT THE INVENTION

1. Alcohol Oxidase

Figure 3:
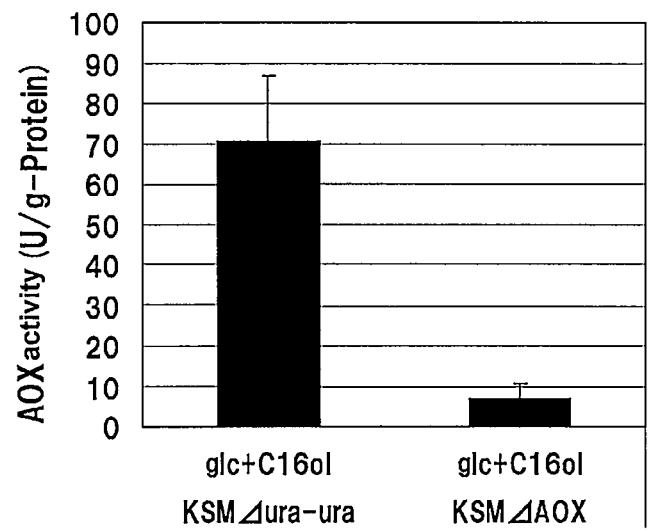
FIG. 3 is a diagram showing alcohol oxidase activity in a KSMΔura-ura strain and a KSMΔAOX strain prepared in Examples.

The protein of the present invention includes the following proteins (a) to (c).
(a) A protein consisting of an amino acid sequence set forth in SEQ ID NO: 1.

(b) A protein consisting of an amino acid sequence having 50% or more identity with the amino acid sequence set forth in SEQ ID NO: 1, and having alcohol oxidase activity.
(c) A protein consisting of an amino acid sequence in which one to several amino acids are subjected to deletion, substitution, insertion or addition in the amino acid sequence set forth in SEQ ID NO: 1, and having alcohol oxidase activity. (Hereinafter, referred to as "the alcohol oxidase of the present invention")

The protein consisting of the amino acid sequence set forth in SEQ ID NO: 1 as shown in the above (a) is a new alcohol oxidase derived from *Candida bombicola*.

Alcohol oxidative enzymes of microorganisms includes an alcohol oxidase (hereinafter, abbreviated also as "AOX") and an alcohol dehydrogenase (ADH), and both catalyze a reaction of oxidizing alcohol to aldehyde. No details of the alcohol oxidative enzyme of *Candida bombicola* have known so far, but the alcohol oxidase and a gene thereof has been identified by the present inventors for the first time. The protein has alcohol oxidase activity as shown in Examples as described later. An amino acid sequence of the alcohol oxidase of *Candida bombicola* is represented in SEQ ID NO: 1, and a nucleotide sequence of the alcohol oxidase gene is represented in SEQ ID NO: 2.

In addition to the above protein (a), the protein of the present invention includes a protein functionally equivalent to the protein (a) such as the protein (b) and the protein (c).

In the protein (b), from a viewpoint of enhancing the productivity of glycolipids, amino acid sequence identity is preferably 80% or more, more preferably 90% or more, and further preferably 95% or more.

The amino acid sequence identity in the present invention means maximum amino acid sequence identity (%) obtained after two amino acid sequences to be compared are subjected to alignment by introducing a gap, when necessary. The amino acid sequence identity can be analyzed by an ordinary method, and for example, can be calculated by blastp of NCBI BLAST (http://blast.ncbi.nlm.nih.gov/) to which a BLAST algorithm is mounted or Homology search to which Genetyx Win is mounted.

In the protein (c), from a viewpoint of enhancing the productivity of glycolipids, one to several amino acids is preferably 1 to 10 amino acids, more preferably 1 to 5 amino acids, and further preferably 1 to 3 amino acids.

The alcohol oxidase activity of these proteins can be confirmed by a method in which a gene encoding the alcohol oxidase protein is destructed to measure the alcohol oxidase activity in the cells, a method in which the alcohol oxidase protein is produced in *E. coli* or the like to measure the alcohol oxidase activity, or the like. In measurement of the alcohol oxidase activity, the method applied in Example as described later, or the like can be applied.

There are no particular limitations on the method for obtaining the protein of the present invention, and the protein may be obtained by chemical techniques or genetic engineering techniques that are conventionally carried out. For example, a natural product-derived protein can be obtained through isolation, purification and the like from a microorganism such as *Candida bombicola*. Furthermore, the protein can also be artificially synthesized based on the information for the amino acid sequence represented by SEQ ID NO: 1, and protein synthesis may be carried out by chemical synthesis, or a recombinant protein may also be produced by gene recombination technologies. In the case of producing a recombinant protein, the alcohol oxidase gene of the present invention that will be described below can be used.

2. Alcohol Oxidase Gene

The gene of the present invention is a gene encoding any one of the proteins (a) to (c) (Hereinafter, referred to as "the alcohol oxidase gene of the present invention").

Specific examples of the gene encoding any one of the proteins (a) to (c) include a gene consisting of any one of DNAs (d) to (f) as follows:
(d) A DNA consisting of a nucleotide sequence set forth in SEQ ID NO: 2;
(e) A DNA consisting of a nucleotide sequence having 50% or more identity with the nucleotide sequence set forth in SEQ ID NO: 2, and encoding a protein having alcohol oxidase activity; and
(f) A DNA capable of hybridizing with a DNA consisting of a nucleotide sequence complementary with the nucleotide sequence set forth in SEQ ID NO: 2 under a stringent condition, and encoding a protein having alcohol oxidase activity.

In the (e), from a viewpoint of enhancing the productivity of glycolipids, nucleotide sequence identity is preferably 80% or more, more preferably 90% or more, and further preferably 95% or more.

The nucleotide sequence identity in the present invention means maximum nucleotide sequence identity (%) obtained after two nucleotide sequences to be compared are subjected to alignment by introducing a gap, when necessary. The nucleotide sequence identity can be analyzed by an ordinary method, and for example, can be calculated by blastn of NCBI BLAST (http://blast.ncbi.nim.nih.gov/) to which a BLAST algorithm is mounted or Homology search to which Genetyx Win is mounted.

The "stringent condition" of the above (f) is, for example, a condition of a southern blotting and the like described in "Molecular Cloning—A LABORATORY MANUAL THIRD EDITION" [Joseph Sambrook, David W. Russell, Cold Spring Harbor Laboratory Press]. It is, for example, a hybridization condition of a gene with a probe by incubation thereof in a solution containing 6×SSC (1×SSC composition: 0.15 M sodium chloride and 0.015 M sodium citrate, pH 7.0), 0.5% SDS, 5×Denhardt and 100 mg/mL herring sperm DNA at 65° C. for 8 to 16 hours.

The method of obtaining the alcohol oxidase gene of the present invention is not particularly limited, and the alcohol oxidase gene can be obtained by conventional genetic engineering techniques. For example, the alcohol oxidase gene of the present invention can be obtained by artificial synthesis based on the amino acid sequence represented by SEQ ID NO: 1 or the nucleotide sequence represented by SEQ ID NO: 2. The artificial synthesis of a gene can be achieved by utilizing the services such as Invitrogen, Inc. Furthermore, the gene can also be obtained by cloning from a microorganism such as *Candida bombicola*, and the cloning can be carried out by, for example, the methods described in Molecular Cloning—A LABORATORY MANUAL THIRD EDITION [Joseph Sambrook, David W. Russell, Cold Spring Harbor Laboratory Press (2001)] and the like.

When mutations are introduced into the amino acid sequence represented by SEQ ID NO: 1 or the nucleotide sequence represented by SEQ ID NO: 2, it can be used a method for introducing site-specific mutation and the like. Examples of the method for introducing site-specific mutation include a method of utilizing the splicing overlap extension (SOE) PCR (Horton et al., Gene 77, 61-68, 1989); the ODA method (Hashimoto-Gotoh et al., Gene, 152, 271-276, 1995); and the Kunkel method (Kunkel, T. A., Proc. Natl. Acad. Sci. USA, 1985, 82, 488). Furthermore, commercially available kits such as the Site-Directed Mutagenesis System Mutan-SuperExpress Km kit (Takara Bio, Inc.), the Transformer™ Site-Directed Mutagenesis kit (Clonetech Laboratories, Inc.), and the KOD-Plus-Mutagenesis kit (Toyobo Co., Ltd.) can also be utilized. Furthermore, the gene containing mutations can also be obtained by introducing genetic mutations at random, and then performing an evaluation of the enzyme activities and a gene analysis thereof by appropriate methods. Specifically, random gene mutations can be introduced by homologous recombination with a DNA fragment that has been randomly cloned, or by irradiating γ-radiation or the like.

3. Transformant

The transformant of the present invention uses a host having a gene encoding any one of the proteins (a) to (c), and the gene in the transformant is subjected to deletion, mutation or repression of gene expression, and the alcohol oxidase activity of the transformant decreases in comparison with the host. In the transformant of the present invention, the alcohol oxidase activity decreases due to the deletion, mutation or repression of the gene, in comparison with the host before transformation. As a result, it is presumed that the alcoholic metabolic pathway in the transformant is inhibited, alcohol used as a raw material of glycolipid synthesis is effectively used for the glycolipid synthesis without being consumed in the alcoholic metabolic pathway, and therefore the productivity of the glycolipid is enhanced.

The transformant of the present invention can be obtained by deleting, mutating or repressing the alcohol oxidase gene in the host.

The host of the transformant only needs to have the gene encoding any one of the proteins (a) to (c). From the viewpoint of enhancing the productivity of glycolipids, the host is preferably a microorganism having the gene encoding any one of the proteins (a) to (c).

The microorganism is preferably yeast, from viewpoints of enhancing handling properties or the productivity of glycolipids. The yeast include fungi belonging to the genus *Candida*, fungi belonging to the genus *Rhodotorula*, fungi belonging to the genus *Pichia*, fungi belonging to the genus *Wickerhamiella*, and fungi belonging to the genus *Starmerella*.

The fungi belonging to the genus *Candida* include *Candida bombicola* (*Starmerella bombicola*), *Candida apicola*, *Candida batistae*, *Candida floricola*, *Candida riodocensis*, and *Candida stellate*.

The fungi belonging to the genus *Rhodotorula*, the fungi belonging to the genus *Pichia*, the fungi belonging to the genus *Wickerhamiella*, or the fungi belonging to the genus *Starmerella* include *Rhodotorula bogoriensis*, *Pichia anomaly PY1*, and *Wickerhamiella domericgiae*.

Among them, from a viewpoint of enhancing the productivity of glycolipids, the fungi belonging to the genus *Candida* are preferred, *Candida bombicola*, *Candida apicola*, *Candida batistae*, *Candida floricola*, *Candida riodocensis*, and *Candida stellata* are more preferred, and *Candida bombicola* is further preferred.

In addition, the above-described host microorganisms can be obtained from biological genetic resource stock centers such as ATCC (American Type Culture Collection) and NBRC (Biological Resource Center, NITE).

The deletion, mutation or repression of the alcohol oxidase gene from a host genome can be conducted by a method of partially or wholly removing a target gene from a genome, or replacing the target gene by other genes, inserting other DNA fragments into the target gene, providing mutation in a transcription or translation initiation region of the target gene, or the like. Among these, a transformant in which the alcohol oxidase gene of the present invention is physically deleted from the host genome is preferable.

The above method of deletion, mutation or repression of gene expression of the alcohol oxidase gene can employ homologous recombination techniques. For example, a linear DNA fragment including an upstream and downstream regions of a target gene in a host genome but including no target gene is constructed by a method such as PCR, and the resultant DNA fragment is incorporated into a host cell to cause double crossover homologous recombination on the side upstream and downstream of the target gene of the host genome, and then the target gene on the genome can be deleted or substituted for other gene fragment. Moreover, a target gene into which mutation such as nucleotide substitution and nucleotide insertion is introduced is constructed by a method such as PCR, and the resulting gene is incorporated into a host cell to cause double crossover homologous recombination in two regions outside the mutation site in the target gene of the host genome, and then a function of the target gene on the genome can be decreased or lost. Moreover, a cyclic recombinant plasmid is prepared by introducing a DNA fragment partially containing a target gene into a suitable plasmid vector, and the resultant plasmid is incorporated into a host cell to cause homologous recombination in part of region of the target gene on the host genome and to split the target gene of the host genome, and then a function of the target gene can be decreased or lost.

The method of deletion, mutation or repression of gene expression of a target gene using homologous recombination can applied with reference to literature such as Besher et al., Methods in molecular biology 47, pp. 291-302, 1995.

Specific examples of methods of introducing DNA fragments or plasmids for homologous recombination into a host cell include a method ordinarily applied to transformation of yeast, such as an electric pulse method, a protoplast method, a lithium acetate method and a modified method thereof.

For example, when the electric pulse method is employed, a host cell that is allowed to grow to a logarithmic growth phase and the DNA fragments or plasmids for homologous recombination are suspended into a sorbitol solution or the like, and an electric pulse may be applied thereto. In the step of mixing the host cell and the DNA fragments or plasmids, it is preferable to add carrier DNA such as Salmon Sperm DNA, polyethylene glycol or the like to the mixture in order to increase a frequency of transformation. Conditions of the electric pulse is preferably adjusted to conditions under which a time constant value (time during which voltage is decayed to about 37% of a maximum value) is about 10 to 20 milliseconds, and a viable cell rate after the pulse becomes about 10 to 40%. After the electric pulse is applied, a cell liquid is spread in a medium containing a sorbitol solution to select transformants.

The selection of transformants with deletion of a target gene can be made by a method of extracting genome DNA from the transformant and performing PCR to amplify a region including the target gene, a southern blotting method using a DNA probe to be bonded with the target gene region, or the like.

The alcohol oxidase activity of the transformant of the present invention decreases in comparison with the host (more specifically, the host before transformation). From the view point of enhancing the productivity of glycolipids, the alcohol oxidase activity of the transformant is preferably 70% or less, more preferably 50% or less, further preferably 30% or less, still further preferably 20% or less, and still further preferably 10% or less, based on the alcohol oxidase activity of the host. Here, the alcohol oxidase activity can be measured by the method described in Examples.

4. Method of Producing Glycolipids

The method of producing a glycolipid of the present invention uses the above transformant and comprises the following steps (1) and (2):
(1) A step of culturing the above transformant in a medium containing alcohol and sugar; and
(2) A step of collecting a glycolipid from the resulting cultured product.

In the present invention, the culturing of a transformant in a medium includes culturing of a microorganism, animal and plant, or a cell or tissue thereof, and also cultivating of a plant in soil or the like. Moreover, the cultured product includes a medium used for culture, cultivation or the like and a transformant subjected thereto.

The medium in which the transformant is cultured contains alcohol and sugar as raw materials of synthesis of the glycolipid.

From a viewpoint of using the resulting glycolipid as a surfactant, the alcohol has preferably 10 or more and 22 or less carbon atoms, more preferably 12 or more and 18 or less carbon atoms, and further preferably 12 or more and 14 or less carbon atoms. From a similar viewpoint, the alcohol preferably includes primary alcohol or secondary alcohol.

Specific examples of preferred alcohol include primary linear saturated or unsaturated alcohol such as 1-decanol, 1-undecanol, 1-dodecanol, 1-tridecanol, 1-tetradecanol, 1-pentadecanol, 1-hexadecanol, 1-heptadecanol, 1-octadecanol, 1-oleyl alcohol, 1-icosanol and 1-docosanol, and secondary saturated or unsaturated alcohol such as 2-decanol, 2-undecanol, 2-dodecanol, 2-tridecanol, 2-tetradecanol, 2-pentadecanol, 2-hexadecanol, 2-heptadecanol and 2-octadecanol. Above all, 1-undecanol, 1-dodecanol, 1-tridecanol, 1-tetradecanol, 1-pentadecanol, 1-hexadecanol, 2-undecanol, 2-dodecanol, 2-tridecanol, 2-tetradecanol, 2-pentadecanol or 2-hexadecanol is preferred, 1-dodecanol, 1-tridecanol, 1-tetradecanol, 2-dodecanol, 2-tridecanol, 2-tetradecanol or 2-pentadecanol is more preferred, and 1-tetradecanol is further preferred.

From a viewpoint of enhancing availability and handling properties, the sugar is preferably glucose, sucrose, fructose, maltose, starch hydrolysate (starch syrup), cellulose hydrolysate or molasses. Above all, from a viewpoint of using the resulting glycolipid as a surfactant, glucose, maltose or molasses is more preferred, and glucose is further preferred.

A medium component other than the alcohol and the sugar can be appropriately selected according to a kind of host.

For example, when the host is a microorganism, sugar alcohols such as sorbitol and glycerol or organic acids such as citric acid can be used as a carbon source; a yeast extract, ammonium chloride, ammonium nitrate, ammonium phosphate, ammonia water, urea, soybean protein, a malt extract, amino acid, peptone or corn steve liquor can be used as a nitrogen source; a manganese salt, a magnesium salt, a calcium salt, a sodium salt, an iron ion, a copper ion, sulfate or phosphate can be used as inorganic salts; and biotin or inositol can be used as vitamins.

When the host is yeast, in particular, a yeast extract, ammonium chloride, urea or the like is preferably used as a nitrogen source; and magnesium sulfate heptahydrate, sodium chloride, calcium chloride dihydrate, dihydrogen potassium phosphate, hydrogen dipotassium phosphate or the like is preferably used as inorganic salts. An antifoaming agent or the like may be added thereto.

Conditions for culturing the transformant can be appropriately selected according to a kind of host.

For example, when the host is a microorganism, pH of the medium is preferably adjusted to about 2.5 to 9.0. Adjustment of pH can be made using inorganic or organic acid, an alkaline solution, urea, calcium carbonate, ammonia or the like. Culture temperature is preferably about 15 to 35° C., and more preferably about 25 to 32° C. Culture time is preferably about 6 to 200 hours, and more preferably about 24 to 148 hours. Aeration or stirring may be added when necessary.

When the host is yeast, in particular, pH of the medium is preferably adjusted to a range in which the yeast can grow, for example, pH of about 3.0 to 8.0. Culture temperature is preferably about 15 to 35° C., and more preferably about 28 to 32° C. Culture time is preferably about 48 to 148 hours, and culture under shaking or aeration or stirring is preferably made.

The transformant is cultured to produce the glycolipid, and then the resulting glycolipid is collected from a cultured product (cultured transformants, cultured liquid or the like) by isolation, purification, or the like.

A method of isolating and collecting the glycolipid is not particularly limited, and isolation and collection can be made by a method to be ordinarily applied upon isolating glycolipid components from a culture supernatant of a microorganism. For example, a method can be applied, such as adsorption and desorption using a hydrophobic or ion-exchange resin, solid-liquid separation by crystallization and membrane treatment.

According to the production method of the present invention, various kinds of glycolipids can be produced by appropriately selecting the host of the transformant, and kinds of alcohol and sugar to be incorporated into the medium. Specific examples of the glycolipids to be produced by the method of the present invention include an alkyl glycoside, a sophorose lipid and a cellobiose lipid. Above all, an alkyl glycoside (more preferably, an alkyl glycoside or an alkyl sophoroside) or a sophorose lipid is preferred because these are suitable for use in a surfactant.

The glycolipid produced by the production method of the present invention can be used for a detergent or emulsifier as a surfactant, or for a cosmetic as an antibacterial agent, or the like.

With regard to the embodiments described above, also disclosed by the present invention includes a protein, a gene, a method, and a transformant described below.

<1> A transformant, wherein, in a host having a gene encoding any one of the following proteins (a) to (c), the gene is subjected to deletion, mutation or repression of gene expression, and alcohol oxidase activity decreases in comparison with the host:
(a) A protein consisting of an amino acid sequence set forth in SEQ ID NO: 1;
(b) A protein consisting of an amino acid sequence having 50% or more, preferably 80% or more, more preferably 90% or more, and further preferably 95% or more identity with the amino acid sequence set forth in SEQ ID NO: 1, and having alcohol oxidase activity; and
(c) A protein consisting of an amino acid sequence in which one to several amino acids, preferably 1 to 10 amino acids, more preferably 1 to 5 amino acids, and further preferably 1 to 3 amino acids are subjected to deletion, substitution, insertion or addition in the amino acid sequence set forth in SEQ ID NO: 1, and having alcohol oxidase activity.

<2> The transformant according to <1>, wherein the host is a microorganism.
<3> The transformant according to <2>, wherein the host is a yeast.
<4> The transformant according to <3>, wherein the yeast is a fungus belonging to the genus *Candida*.
<5> The transformant according to <4>, wherein the fungus belonging to the genus *Candida* is selected from the group consisting of *Candida bombicola, Candida apicola, Candida batistae, Candida floricola, Candida riodocensis* and *Candida stellate*.
<6> The transformant according to <5>, wherein the fungus belonging to the genus *Candida* is *Candida bombicola*.
<7> The transformant according to any one of <1> to <6>, wherein alcohol oxidase activity of the transformant is 70% or less, preferably 50% or less, more preferably 30% or less, further preferably 20% or less, and still further preferably 10% or less based on alcohol oxidase activity of the host.
<8> A method of producing a glycolipid, comprising the following steps (1) and (2):
(1) A step of culturing the transformant according to any one of <1> to <7> in a medium containing alcohol and sugar; and
(2) A step of collecting a glycolipid from the resulting cultured product.
<9> The method of producing a glycolipid according to <8>, wherein the alcohol includes primary or secondary alcohol having 10 or more, preferably 12 or more, and 22 or less, preferably 18 or less, more preferably 14 or less carbon atoms.
<10> The method of producing a glycolipid according to <8> or <9>, wherein the glycolipid is an alkyl glycoside or a sophorose lipid.
<11> A gene encoding any one of the above proteins (a) to (c).
<12> The gene according to <11>, which consists of any one of the following DNAs (d) to (f):
(d) A DNA consisting of a nucleotide sequence set forth in SEQ ID NO: 2;
(e) A DNA consisting of a nucleotide sequence having 50% or more, preferably 80% or more, more preferably 90% or more, and further preferably 95% or more identity with the nucleotide sequence set forth in SEQ ID NO: 2, and encoding a protein having alcohol oxidase activity; and
(f) A DNA capable of hybridizing with a DNA consisting of a nucleotide sequence complementary with the nucleotide sequence set forth in SEQ ID NO: 2 under a stringent condition, and encoding a protein having alcohol oxidase activity.
<13> A protein selected from the above (a) to (c).
<14> Use of the transformant according to any one of <1> to <7> for the production of a glycolipid.
<15> The use of the transformant according to <14>, wherein the glycolipid is produced by a method comprising the following steps (1) and (2):
(1) A step of culturing the transformant according to any one of <1> to <7> in a medium containing alcohol and sugar; and
(2) A step of collecting a glycolipid from the resulting cultured product.
<16> The use of the transformant according to <15>, wherein the alcohol includes primary or secondary alcohol having 10 or more, preferably 12 or more, and 22 or less, preferably 18 or less, more preferably 14 or less carbon atoms.
<17> The use of the transformant according to any one of <14> to <16>, wherein the glycolipid is an alkyl glycoside or a sophorose lipid.

EXAMPLES

Hereinafter, the present invention will be described more in detail with reference to Examples, but the present invention is not limited thereto.
[Medium and Culture Condition]
Yeast belonging to the genus *Candida* was cultured using the following medium. Each medium was subjected to autoclaving at 121° C. for 20 minutes and then mixed and used.
As preculture, a culture liquid subjected to shaking culture at 30° C., 250 rpm and for 48 hours in a 24 mm$\phi$×200 mm large test tube (charged, 5 mL of YPD medium) was inoculated at 2% (v/v) into a 24 mm$\phi$×200 mm large test tube (charged, 5 mL of AG production medium) and subjected to shaking culture at 30° C. and 250 rpm.
YPD medium: 1% (D)-glucose, 1% Bacto™ Yeast Extract (manufactured by Nippon BD Co., Ltd.), 1% Bacto™ Tryptone (manufactured by Nippon BD Co., Ltd.)
AG production medium: 15% (D)-glucose, 0.41% trisodium citrate (anhydrous), 0.4% Bacto™ Yeast Extract, 0.154% ammonium chloride, 0.07% magnesium sulfate heptahydrate, 0.05% sodium chloride, 0.027% calcium chloride dihydrate, 0.1% dihydrogen potassium phosphate, 0.012% hydrogen dipotassium phosphate (adjusted to pH 5.8 by 1 M HCL)
Minimum medium: 0.68% Yeast nitrogen base without amino acids (manufactured by Nippon BD Co., Ltd.), 2% (D)-glucose
Alcohol utilizing medium: 0.68% Yeast nitrogen base without amino acids (manufactured by Nippon BD Co., Ltd.), 0.05% Bacto™ Yeast Extract, 2% carbon source
[Extraction of Genome DNA]
Genome DNA of *Candida bombicola* was extracted using Dr. GenTLE (for yeast) High Recovery (manufactured by Takara Bio Inc.) from cells collected by centrifuging, at 4° C. and 15,000 rpm for 1 minute, of a cultured liquid subjected to shaking culture at 30° C. and 250 rpm for 48 hours in a 24 nnrmp×200 mm large test tube (charged, YPD medium, 5 mL).
[PCR]
PCR was conducted using PrimeStar Max DNA Polymelase (manufactured by Takara Bio Inc.) according to an attached protocol.

Example

1. EST Analysis of *Candida bombicola*

A *Candida bombicola* NBRC10243 strain was obtained from NBRC (Biological Resource Center, NITE). One platinum loop of *Candida bombicola* was inoculated into a 100 mL-volume test tube containing 5 mL of 50 g/L YPD Broth (manufactured by Nippon BD Co., Ltd.), and cultured at 30° C. and 250 rpm for 48 hours. The resulting precultured liquid was inoculated, at 2%, into 5 mL of SL medium (10% (D)-glucose, 10% ethyl palmitate (manufactured by Tokyo Chemical Industry Co., Ltd), 1% urea, 0.5% Bacto™ Yeast Extract (manufactured by Nippon BD Co., Ltd.), adjusted to pH 5.0 by hydrochloric acid). As a culture vessel, a 100 mL test tube was used, and culture was made at 30° C. and 250 rpm. Cultured cells after 48 hours in culture was used as RNA source for preparing cDNA.

RNA was extracted from the sampled cells using RNeasy Mini Kit (manufactured by QIAGEN) by a method in which the protocol attached to the kit was partially modified. Cell walls were dissolved by adding 1 mL of Buffer Y1 to the cells and shaking the resulting solution at 30° C. for 30 minutes. In this step, Zymolyase-20T was added to the Buffer Y1 be 100 U/mL. Full-length cDNA library was synthesized from the resulting RNA using a SMARTer cDNA synthesis kit (manufactured by Clontech Laboratories, Inc.). EST analysis was consigned to Genaris, Inc. to obtain cDNA sequence information and annotation data.

The obtained DNA sequences were subjected to homology search for alcohol oxidase homologs. As a result, no sequence exhibiting high homology with known alcohol oxidase was found, but one sequence exhibiting low homology, 35% identity as an amino acid sequence homology, with AOX2 derived from *Candida tropicalis* (Genbank: AAS46880.1) was found. This nucleotide sequence was represented in SEQ ID NO: 2, and a gene consisting of this nucleotide sequence was named as a 900c 0002 gene. The amino acid sequence encoded by the gene was represented in SEQ ID NO: 1.

Next, the 900c 0002 gene was searched from a *Candida bombicola* KSM36 strain (FERM-BP 799). As a result, the KSM36 strain also was found to have a gene having a sequence exactly identical with the nucleotide sequence represented by SEQ ID NO: 1.

2. Deletion of 900c 0002 Gene (1) Construction of Uracil Gene Mutant Strain of *Candida bombicola*

A uracil auxotrophic strain was selected from the *Candida bombicola* KSM36 strain according to a technique described in Van Bogaert et al., Yeast (2008), 25, pp. 273-278. Further, a strain into which mutation was inserted into an ura3 gene region was selected from the uracil auxotrophic strains and taken as a KSMΔura3 strain.

Subsequently, sequence analysis of the ura3 gene region of the KSM36 strain, the NBRC10243 strain and the KSMΔura3 strain was conducted. As a result, the ura3 gene sequence of the KSM36 strain was identical with the ura3 gene sequence of the NBRC10243 strain (GenBank Accession No. DQ916828), and the ura3 gene sequence of the KSMΔura3 strain had a mutation that cysteine (Cys) at 54-position was changed to tyrosine (Tyr) by single nucleotide mutation (FIG. 1).

The KSMΔura3 strain was not allowed to grow in the minimum medium, but was grown in a YPD medium to which 5-fluoroorotic acid was added and in a minimum medium to which uracil was added. Moreover, when a wild type ura3 gene derived from the NBRC10243 strain was transferred into the KSMΔura3 strain by the above described technique by Van Bogaert et al., such a strain was grown in the minimum medium. Moreover, when uracil was added to the medium, the KSMΔura3 strain showed the productivity of sophorose lipids equal to that of the parent KSM36 strain.

(2) Construction of Plasmid for Deletion of 900c 0002 Gene

A plasmid for deletion of the 900c 0002 gene, pUC-ΔAOX, was constructed by the following technique.

Then, pUC-ΔAOX has a sequence complementary with about 1000 bp of sequence upstream of the 900c 0002 gene and a sequence complementary with about 1000 bp of sequence downstream of the 900c 0002 gene, and the ura3 gene inserted between these sequences.

DNA fragments of the region of about 1000 bp upstream of the 900c 0002 gene, the region of about 1000 bp downstream of the 900c 0002 gene, and the ura3 gene were amplified by PCR using genome DNA extracted from the *Candida bombicola* KSM36 strain as a template and PCR primers of AOX1 US in F1 (5'-AGCTTGCATGCCTGCTT-TAAATCCAGAAAGAACTG-3') (SEQ ID NO: 3) and AOX1 US-ura R (5'-CGAAAAATATGTACTGATAACT-GCGTCAGTCATTG-3') (SEQ ID NO: 4), Pura3 F (5'-AGTACATATTTTTCGAAACAGCTCGCAA-3') (SEQ ID NO: 5) and ura3 R (5'-CTAAGAAACTCATCTTGACT-GAACTTTTC-3') (SEQ ID NO: 6), or ura-AOX1 LS F (5'-AGATGAGTTTCTTAGAAGCCTTATATCGAATA-CAC-3') (SEQ ID NO: 7) and AOX1 LS in R1 (5'-ATTC-GAGCTCGGTACGACACTTCTCAGGAACCCTC-3') (SEQ ID NO: 8).

Next, a region derived from a plasmid pUC118 was amplified using the plasmid pUC118 as a template and PCR primers of pUC in F2 (5'-GTACCGAGCTCGAATTCGT-3') (SEQ ID NO: 9) and pUC in R2 (5'-GCAGGCATG-CAAGCTTGGC-3') (SEQ ID NO: 10). The amplified product was bonded with the above-amplified DNA fragments by using Infusion HD Cloning Kit (manufactured by Clontech Laboratories, Inc.). The resulting plasmid was transferred into *E. coli* DH5α strain, and cultured on an LB agar medium containing 100 ppm of ampicillin sodium salt, and then grown colonies were separated as a transformant. A plasmid was extracted from the transformant to obtain a target plasmid for deletion of 900c 0002 gene, pUC-ΔAOX.

(3) Construction of 900c 0002 Gene Deletion Strain of *Candida bombicola*

According to a technique by M. D. DE. Backer et al., Yeast (1999), 15, p. 1609-1618, the KSMΔura3 strain was transformed using the pUC-ΔAOX. Specifically, the KSMΔura3 strain was inoculated into 5 mL of YPD medium containing 300 ppm of uracil, and precultured at 30° C. and 250 rpm for 48 hours. Then, 0.5 mL of cultured liquid was seeded into 50 mL of YPD medium containing 300 ppm of uracil, and cultured at 30° C. and 120 rpm for about 6 hours. Grown cells were collected, and then the cells were washed twice using 20 mL of ice-cooled sterilized water. The cells were suspended into 1 mL of ice-cooled 1 M sorbitol solution, the resulting suspension was centrifuged at 5,000 rpm for 5 minutes, and a supernatant was discarded, and then 400 µL of 1 M sorbitol was added thereto, and suspended. The resulting cell suspension was dispensed by 50 µL for each, and 2.5 µg of pUC-ΔAOX was added thereto. The cell suspension was subjected to electroporation using BIO-RAD GENE PULSER II (manufactured by Bio-Rad Laboratories, Inc.), and then the resulting material was spread into a minimum medium containing 1 M sorbitol, and cultured at 30° C. for one week.

From the resulting transformant, strains in which homologous recombination by double crossover in regions upstream and downstream of the 900c 0002 gene occurred were selected according to a PCR method. Specifically, PCR was carried out using genome DNA extracted from the transformant, and primers of AOX1 US in F1 (5'-AGCTTGCAT-GCCTGCTTTAAATCCAGAAAGAACTG-3') (SEQ ID NO: 3) and AOX1 LS in R1 (5'-ATTCGAGCTCGGTAC-GACACTTCTCAGGAACCCTC-3') (SEQ ID NO: 8). As a result, the homologous recombinant strains by the double crossover were obtained at a probability of 70% per the transformants, and were taken as a KSMΔAOX strain.
{0046}
(4) Construction of Uracil Gene Transfer Strain of *Candida bombicola*

As a control strain relative to the 900c 0002 gene deletion strain, a strain was prepared in which a wild type ura3 gene was transferred into the mutated ura3 region of a KSMΔura strain and the 900c 0002 gene was not deleted.

A DNA fragment of a ura3 region was amplified by PCR using the genome DNA extracted from the *Candida bombicola* KSM36 strain as a template and primers of Pura3 F (5'-AGTACATATTTTTCGAAACAGCTCGCAA-3') (SEQ ID NO: 5) and ura3 R2 (5'-TTCATCATCGTCACTATA-3') (SEQ ID NO: 11). The resulting DNA fragment was inserted into pUC118DNA HincII/BAP (manufactured by Takara Bio Inc.) using Mighty Cloning Reagent Set Blunt End (manufactured by Takara Bio Inc.) to obtain a plasmid pUC-ura3.

The plasmid pUC-ura3 was transferred into the KSMΔura strain according to a technique similar to the technique in (3) described above. To confirm homologous recombination, PCR was carried out using genome DNA extracted from the transformant, and primers corresponding to regions derived from the plasmid, pUC seq 1 (5'-GGCGAAAGGGGGAT-GTGC-3') (SEQ ID NO: 12) and pUC seq 2 (5'-GCAC-CCCAGGCTTTACAC-3') (SEQ ID NO: 13). As a result, the homologous recombinant strains by the double crossover were obtained at a probability of 11% per the resulting transformants, and were taken as a KSMΔura-ura strain.

3. Alcohol Utilizing Ability of KSMΔAOX Strain

The KSMΔura-ura strain and the KSMΔAOX strain of *Candida bombicola* were precultured in the YPD medium at 30° C. and 250 rpm for 48 hours. A precultured liquid was inoculated at 0.01% for each in an alcohol utilizing medium containing as a carbon source any of (D)-glucose, 1-tetradecanol, 1-hexadecanol and 2-tetradecanol, or in a medium containing no carbon source, and cultured at 30° C. and 250 rpm to measure a viable cell count. FIG. 2 shows a relationship between culture time and a viable cell count. In FIG. 2, "glc" shows use of (D)-glucose, "C14ol" shows use of 1-tetradecanol, "C16ol" shows use of 1-hexadecanol, and "2-C14ol" shows use of 2-tetradecanol as the carbon source, respectively.

As is obvious from FIG. 2, both the KSMΔura-ura strain and the KSMΔAOX strain were not grown in the medium containing no carbon source, but were grown in a glucose-added medium. These results indicated that both the KSMΔura-ura strain and the KSMΔAOX strain use glucose as a carbon source.

When alcohol was used as a carbon source, the KSMΔura-ura strain was grown in a medium containing 1-tetradecanol, 1-hexadecanol or 2-tetradecanol. On the other hand, the KSMΔAOX strain was not grown in the medium containing any of 1-tetradecanol, 1-hexadecanol and 2-tetradecanol.

These results showed that the KSMΔura-ura strain oxidizes alcohol into aldehyde and can utilize the alcohol as a carbon source, but the KSMΔAOX strain loses alcohol utilizing ability and cannot utilize alcohol as a carbon source.

4. Measurement of Alcohol Oxidase Activity

The KSMΔura-ura strain and the KSMΔAOX strain of *Candida bombicola* were precultured in the YPD medium at 30° C. and 250 rpm for 48 hours. A precultured liquid was inoculated at 1% in an alcohol utilizing medium to which (D)-glucose and 1-hexadecanol were added at 10 g/L for each, and cultured at 30° C. and 250 rpm for 48 hours. A microsomal membrane protein fraction was prepared from the cultured cell to measure alcohol oxidase activity (AOX activity). Alcohol oxidases of microorganisms are known to be localized in a membrane protein fraction.

The preparation of the microsomal membrane protein fraction and measurement of the alcohol oxidase activity were carried out according to the method described in G. D. Kemp et al., Appl. Microbiol. Biotechnol. (1988), 29, p. 370-374.

[Preparation of Microsomal Membrane Protein Fraction]

20 mL of the cultured cells was centrifuged at 8,000 rpm and 4° C. for 10 minutes and collected, and then the cells were washed twice with 10 mL of normal saline. The cells were suspended by adding 500 μL of $\frac{1}{15}$ M phosphate buffer (pH 7.4), and crushed using Multi-beads shocker (manufactured by Yasui Kikai Corporation), and using 0.5 mm glass beads as media. Then, 500 μL of $\frac{1}{15}$ M phosphate buffer (pH 7.4) was added and mixed, and a crushed liquid was centrifuged at 4° C. for 5 minutes at 3,000 g to eliminate uncrushed cells. A supernatant was centrifuged at 4° C. for 60 minutes at 20,000 g to eliminate a mitochondria fraction and a peroxisome fraction. A remaining supernatant was collected and centrifuged at 4° C. for 90 minutes at 100,000 g, and then the resulting precipitate was collected and suspended by adding 200 μL of $\frac{1}{15}$ M phosphate buffer (pH 7.4). This suspension was used as the microsomal membrane protein fraction for measurement of the alcohol oxidase activity as described below.

[Measurement of Alcohol Oxidase Activity]

100 μL of 0.1 M phosphate buffer (pH 7.4), 50 μL of 2.8 g/L 2,2'-azino-di[3-ethylbenzothiazoline-(6)-sulfonic acid] (ABTS) solution, 30 μL of horseradish peroxidase 47 units/mL solution, and 10 μL of microsomal membrane protein fraction were mixed and incubated at 30° C. for 5 minutes. Then, 10 μL of 5 mM 1-dodecanol DMSO solution was added thereto to measure absorbance at 405 nm in 0 minutes and after 5 minutes. Alcohol oxidases oxidize 1 μmol of alcohol to produce 2 μmol of radical cation. 1 mM of radical cation type ABTS shows an absorbance of 18.4 at 405 nm, which corresponds to 0.5 mM of oxidized substrate. Therefore, a variation of absorbance of 0.0368 per minute was defined as 1 U of alcohol oxidase.

FIG. 3 shows alcohol oxidase activity per g of microsomal protein.

As is obvious from FIG. 3, the alcohol oxidase activity of the KSMΔAOX strain with deletion of the 900c 0002 gene significantly decreased in comparison with the KSMΔura-ura strain. This result indicates that the 900c 0002 gene isolated in the above item 1. is a new alcohol oxidase gene acting on long-chain alcohol.

5. Conformation of Enzyme Activity by Heterologous Expression of 900c 0002 Gene

A DNA fragment of the 900c 0002 gene was amplified by PCR using the genome DNA extracted from the *Candida bombicola* KSM36 strain as a template, and primers of AOX F (5'-gaaggagatatacatatgactgacgcagttatcctc-3') (SEQ ID NO: 14) and AOX R (5'-agtgcggccgcaagctagcttagtttgaagcttag-3') (SEQ ID NO: 15). Moreover, a DNA fragment was amplified by PCR using a plasmid pET21a (manufactured by Novagen, Inc.) as a template, and primers of pET21 F (5'-gcttgcggccgcactcgag-3') (SEQ ID NO: 16) and pET21 R (5'-atgtatatctccttcttaaag-3') (SEQ ID NO: 17). The resulting two DNA fragments were fused using In-Fusion HD Cloning Kit (manufactured by Takara Bio Inc.) to obtain a plasmid pET-AOX.

The plasmid pET-AOX was transferred into *E. coli* BL21 (DE3) (manufactured by Funakoshi Corporation) to obtain a BL21(DE3)-pET-AOX strain. Moreover, as a control strain, a BL21(DE3)-pET strain in which the plasmid pET21a was transferred into *E. coli* BL21(DE3) was prepared.

These recombinant strains were cultured in an LB medium containing 100 ppm of ampicillin sodium salt (manufactured by Wako Pure Chemical Industries, Ltd.) at 37° C. and 250 rpm for 12 hours, and then inoculated at 1% in the LB medium containing 100 ppm of ampicillin sodium salt, and cultured at 37° C. and 250 rpm for 2.5 hours. Subsequently, a 1 M IPTG solution was added thereto to be 0.1 mM in a final concentration, and cultured at 25° C. and 250 rpm for 16 hours. Then, 5 mL of cultured cells was centrifuged at 15,000 rpm and 4° C. for 2 minutes and collected, and then the cells were washed twice with 1 mL of normal saline. The cells were suspended by adding 500 μL of 1/15 M phosphate buffer (pH 7.4), and crushed using Multi-beads shocker (manufactured by Yasui Kikai Corporation), and using 0.5 mm glass beads. A crushed liquid was centrifuged at 4° C. and 15,000 rpm for 5 minutes to eliminate uncrushed cells. A remaining supernatant was collected to conduct a protein concentration analysis, an SDS polyacryl amide electrophoresis analysis (SDS-PAGE) and carry out measurement of alcohol oxidase activity.

The protein concentration analysis was conducted out using Bio-Rad Protein Assay Kit (manufactured by Bio-Rad Laboratories, Inc.), and bovine serum albumin (manufactured by Bio-Rad Laboratories, Inc.) as a reference material, and SDS-PAGE was conducted using Mini-PROTEAN TGX GEL AnykD (manufactured by Bio-Rad Laboratories, Inc.) by means of Mini-PROTEAN 3 Ready Gel Cell (manufactured by Bio-Rad Laboratories, Inc.). A sample was diluted 3 times with a Laemmli sample buffer (manufactured by Bio-Rad Laboratories, Inc.), held at 100° C. for 5 minutes to allow thermal denaturation, and then provided for a gel. A premix buffer (10×tris/glycin/SDS (manufactured by Bio-Rad Laboratories, Inc.)) was diluted 10 times with deionized water and taken as a electrophoresis liquid to allow electrophoresis at a constant voltage of 200 V per sheet for about 30 minutes. A gel after electrophoresis was stained by Bio-Safe CBB G-250 Stain (manufactured by Bio-Rad Laboratories, Inc.).

Figure 4:
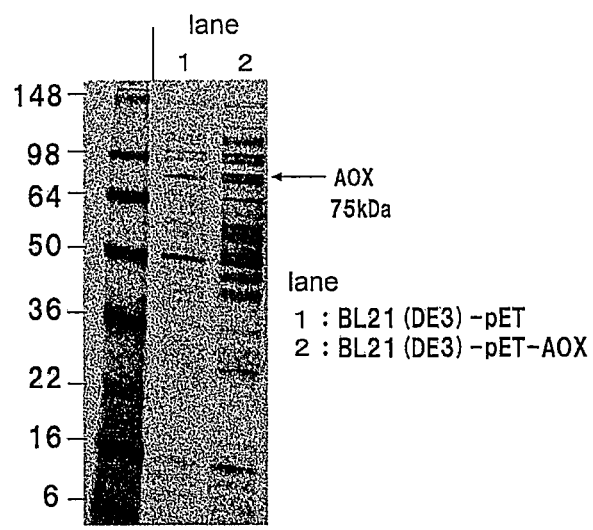
FIG. 4 is a diagram showing the results of detecting an expressed protein in a BL21(DE3)-pET-AOX strain and a BL21(DE3)-pET strain prepared in Examples.

FIG. 4 shows the results of electrophoresis. In FIG. 4, lane 1 shows a BL21(DE3)-pET strain being the control strain, and lane 2 shows a BL21(DE3)-pET-AOX strain into which a 900c 0002 gene was transferred, respectively.

Figure 5:
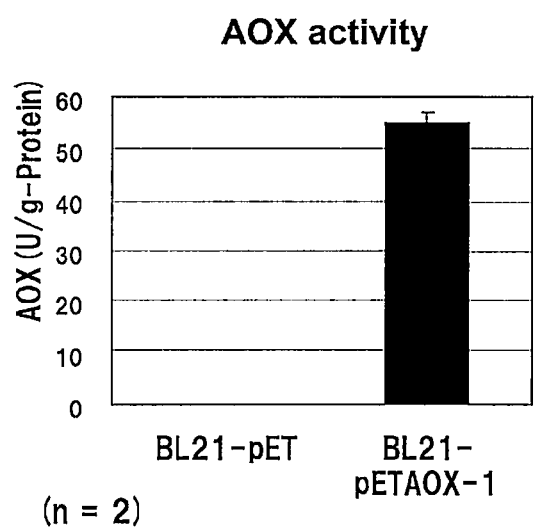
FIG. 5 is a diagram showing alcohol oxidase activity in a BL21(DE3)-pET-AOX strain and a BL21(DE3)-pET strain.

Measurement of alcohol oxidase activity was carried out in a manner similar to the procedures in the above item 4. In addition, as a substrate for measuring activity, 1-dodecanol was used. FIG. 5 shows the results.

As is obvious from FIG. 4, in the BL21(DE3)-pET-AOX strain into which the 900c 0002 gene was transferred, a band was detected in a position of 75 kDa and expression of the 900c 0002 gene was confirmed. On the other side, in the BL21(DE3)-pET strain into which no 900c 0002 gene was transferred, no band was confirmed in the position.

Moreover, from FIG. 5, the alcohol oxidase activity was confirmed in the BL21(DE3)-pET-AOX strain into which the 900c 0002 gene was transferred and expressed. On the other side, no alcohol oxidase activity was confirmed in the BL21(DE3)-pET strain.

These results indicate that the 900c 0002 gene isolated in the above item 1. is a new alcohol oxidase gene acting on long-chain alcohol.

6. Glycolipid Productivity of KSMΔAOX Strain

The KSMΔura-ura strain and the KSMΔAOX strain were precultured in the YPD medium at 30° C. and 250 rpm for 48 hours. A precultured liquid was inoculated at 2% into a 500 mL Sakaguchi flask into which 30 mL of AG production medium was charged, and then cultured at 30° C. and 120 rpm for 48 hours, and then 1-tetradecanol as a substrate was added thereto to be 10 g/L.

A cultured liquid after being cultured for 72 hours from addition of the substrate was provided for the following LC-MS analysis and GC analysis.

[LC-MS Analysis]

As an apparatus, UFLC 20A-LCMS 2020 (manufactured by Shimadzu Corporation) was used, and as a column, L-column ODS 4.6×150 mm, 5 μm (Chemicals Evaluation and Research Institute, Japan) was used. For an eluent A, a 0.01 M ammonium acetate aqueous solution was used, and for an eluent B, a 0.01 M ammonium acetate methanol solution was used, and measurement was carried out at a flow rate of 1 mL/min, at a column oven temperature of 40° C. and based on a time program of 50% (5 minutes) to 20%/min to 90% to 95% (5 minutes) to 100% (30 minutes). Detection was conducted in a negative ion mode.

As a result of LC-MS analysis, no peak of mobility (10.06 minutes) close to the mobility of dodecyl maltoside was observed in the KSMΔura-ura strain. On the other hand, a peak was conformed at mobility close to the mobility of dodecyl maltoside in the KSMΔAOX strain, and in the negative mode, a peak at 10.068 minutes corresponded to a molecular weight of 579.5 [M-H], and a peak at 11.275 minutes corresponded to a molecular weight of 621.5 [M-H].

The fact that a molecular weight of acetyl tetradecyl maltoside is 580.3 and a molecular weight of diacetyl tetradecyl maltoside is 622.5, and a description by S. Fleurackers et al., Eur. J. Lipid Sci. Technol. (2010), 112, pp. 655-662 suggest that the peak at 10.068 minutes is acetyl tetradecyl sophoroside shown in the following structural formula 1 (1-O-tetradecyl-(2'-O-β-D-glucopyranosyl-β-D-glucopyranoside) 6'acetate), and the peak at 11.275 minutes is acetyl tetradecyl sophoroside shown in the following structural formula 2 (1-O-tetradecyl-(2'-O-β-D-glucopyranosyl-β-D-glucopyranoside)6',6"diacetate).

{Chemical formula 1}

Structural formula 1

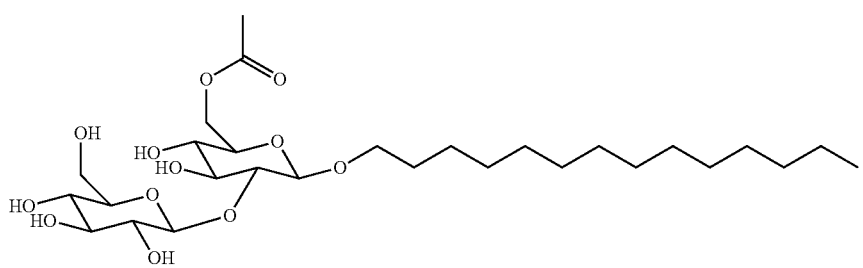

{Chemical formula 2}

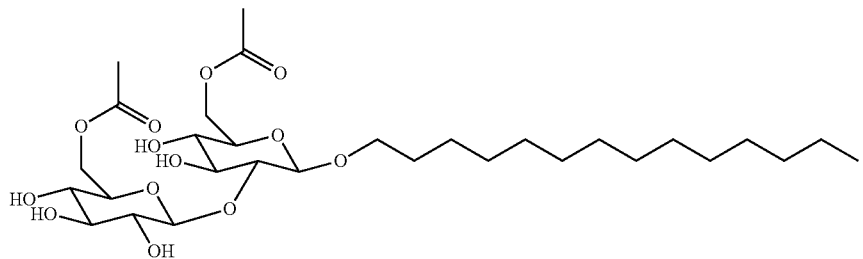

Structural formula 2

[GC Analysis]

5 mL of cultured liquid was subjected to extraction twice with 2.5 mL of 1-buthanol containing 0.05% of 1-octadecanol as an internal standard. Next, the resulting extract was dried to solid by means of a centrifugal evaporator, and then 1 M NaOH aqueous solution was added thereto, and the resulting mixture was treated at 100° C. for 4 hours. Subsequently, extraction was carried out twice with 2.5 mL of 1-butanol, and then the resulting extract was dried to solid by means of a centrifugal evaporator, and converted into a derivative using a trimethylsilylating (TMS) reagent. A trimethylsylilated sample was analyzed by the following GC-FID method to obtain a glycolipid content and a remaining substrate content.

GC was conducted by using as an apparatus 7890A (manufactured by Agilent Technologies, Inc.), as a column, DB-1 ms 25 m×0.20 mm×330 μm (manufactured by J&W Scientific, Inc.), and high-purity helium for a mobile phase, and at a flow rate of 1 mL/min and based on a temperature rise program of 100° C. (1 minute) to 10° C./min to 300° C. (10 minutes). As a standard material, n-dodecyl maltoside (manufactured by CALBIOCHEM, Inc.) was used and peaks arisen from alkyl glycoside detected from 18 minutes to 19.5 minutes were integrated and calculated as an alkyl glucoside content.

Figure 6:
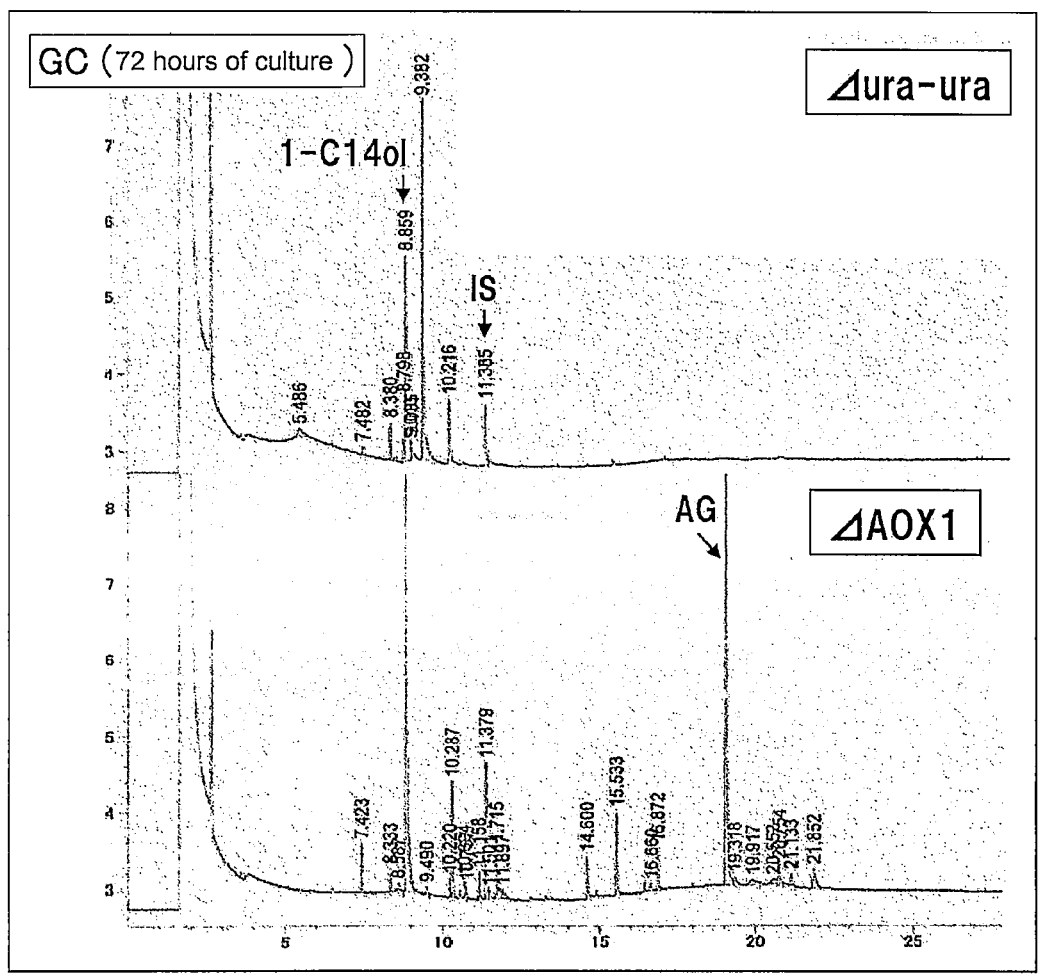
FIG. 6 is a diagram showing the results of GC analysis of a culture liquid in which a KSMΔura-ura strain and a KSMΔAOX strain prepared in Examples are cultured in a culture media containing 1-tetradecanol as a substrate.

FIG. 6 shows the results of GC analysis. In FIG. 6, 1-C14ol shows a peak of 1-tetradecanol, IS shows a peak of 1-octadecanol that was used as the internal standard and AG shows a peak of alkyl glucoside, respectively.

As a result of the GC analysis, no peak of mobility close to the mobility of dodecyl maltoside (18.509 minutes) was observed in the KSMΔura-ura strain. On the other hand, a new peak was recognized at 19.063 minutes in the KSMΔAOX strain. At this peak, yield was 3.7 g/L in dodecyl maltoside equivalent.

This result showed that the KSMΔura-ura strain produces almost no alkyl glycoside even when alcohol and sugar are added as a substrate, but the KSMΔAOX strain produces alkyl glycosides from alcohol and sugar.

The results described above showed that the KSMΔAOX strain can produce a glycolipid such as alkyl glycoside and tetradecyl sophoroside at high yield from glucose and 1-tetradecanol as a substrate.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2012-230994 filed in Japan on Oct. 18, 2012, which is entirely herein incorporated by reference.

The invention claimed is:

1. A transformant of a host, the host having a gene encoding any one of the following proteins (a) to (c), wherein, in the transformant, the gene is deleted, mutated or subject to repression of gene expression, and wherein, in the transformant, as a result of the gene being deleted, mutated or subject to repression of gene expression, alcohol oxidase activity is decreased as compared to that in the host,
wherein, proteins (a) to (c) are:
   (a) A protein consisting of an amino acid sequence set forth in SEQ ID NO: 1;
   (b) A protein consisting of an amino acid sequence having 90% or more identity with the amino acid sequence set forth in SEQ ID NO: 1, and having alcohol oxidase activity; and
   (c) A protein consisting of an amino acid sequence in which one to ten amino acids in the amino acid sequence set forth in SEQ ID NO: 1 have been deleted, substituted, inserted or added, and having alcohol oxidase activity.

2. The transformant according to claim 1, wherein the host is a microorganism.

3. The transformant according to claim 2, wherein the host is a yeast.

4. The transformant according to claim 3, wherein the yeast is a fungus belonging to the genus *Candida*.

5. The transformant according to claim 4, wherein the fungus belonging to the genus *Candida* is selected from the group consisting of *Candida bombicola, Candida apicola, Candida batistae, Candida floricola, Candida riodocensis* and *Candida stellate*.

6. The transformant according to claim 1, wherein the alcohol oxidase activity in the transformant is 70% or less that of the host.

7. The transformant according to claim 1, wherein protein (b) is a protein consisting of an amino acid sequence having 95% or more identity with the amino acid sequence set forth in SEQ ID NO: 1, and having alcohol oxidase activity.

8. The transformant according to claim 1, wherein protein (c) is a protein consisting of an amino acid sequence in which one to five amino acids have been deleted, substituted, inserted or added in the amino acid sequence set forth in SEQ ID NO: 1, and having alcohol oxidase activity.

9. The transformant according to claim 1, wherein the gene encoding any one of the proteins (a) to (c) is a gene consisting of any one of the following DNAs (d) to (f):
  (d) A DNA consisting of a nucleotide sequence set forth in SEQ ID NO: 2;
  (e) A DNA consisting of a nucleotide sequence having 90% or more identity with the nucleotide sequence set forth in SEQ ID NO: 2, and encoding a protein having alcohol oxidase activity; and
  (f) A DNA capable of hybridizing with a DNA consisting of a nucleotide sequence complementary with the nucleotide sequence set forth in SEQ ID NO: 2 under stringent conditions, and encoding a protein having alcohol oxidase activity, wherein the stringent conditions comprise incubation in a solution containing 6×SSC, 0.5% SDS, 5×Denhardt and 100 mg/mL herring sperm DNA at 65° C. for 8 to 16 hours and in which a 1×SSC composition contains 0.15 M sodium chloride and 0.015 M sodium citrate at pH 7.0.

10. The transformant according to claim 9, wherein DNA (e) is a DNA consisting of a nucleotide sequence having 95% or more identity with the nucleotide sequence set forth in SEQ ID NO: 2, and encoding a protein having alcohol oxidase activity.

11. A method of producing a glycolipid, comprising the following steps (1) and (2):
  (1) A step of culturing the transformant according to claim 1 in a medium containing alcohol and sugar; and
  (2) A step of collecting a glycolipid from the resulting cultured product.

12. The method of producing a glycolipid according to claim 11, wherein the alcohol includes a primary or secondary alcohol having 10 or more and 22 or less carbon atoms.

13. The method of producing a glycolipid according to claim 11, wherein the glycolipid is an alkyl glycoside or a sophorose lipid.

14. The method of producing a glycolipid according to claim 11, wherein the alcohol oxidase activity of the transformant is 70% or less that of the host.

15. The method of producing a glycolipid according to claim 11, wherein protein (b) is a protein consisting of an amino acid sequence having 95% or more identity with the amino acid sequence set forth in SEQ ID NO: 1, and having alcohol oxidase activity.

16. The method of producing a glycolipid according to claim 11, wherein protein (c) is a protein consisting of an amino acid sequence in which one to five amino acids have been deleted, substituted, inserted or added in the amino acid sequence set forth in SEQ ID NO: 1, and having alcohol oxidase activity.

17. The method of producing a glycolipid according to claim 11, wherein the gene encoding any one of the proteins (a) to (c) is a gene consisting of any one of the following DNAs (d) to (f):
  (d) A DNA consisting of a nucleotide sequence set forth in SEQ ID NO: 2;
  (e) A DNA consisting of a nucleotide sequence having 90% or more identity with the nucleotide sequence set forth in SEQ ID NO: 2, and encoding a protein having alcohol oxidase activity; and
  (f) A DNA capable of hybridizing with a DNA consisting of a nucleotide sequence complementary with the nucleotide sequence set forth in SEQ ID NO: 2 under stringent conditions and encoding a protein having alcohol oxidase activity, wherein the stringent conditions comprise incubation in a solution containing 6×SSC, 0.5% SDS, 5×Denhardt and 100 mg/mL herring sperm DNA at 65° C. for 8 to 16 hours and in which a 1×SSC composition contains 0.15 M sodium chloride and 0.015 M sodium citrate at pH 7.0.

18. The method of producing a glycolipid according to claim 17, wherein DNA (e) is a DNA consisting of a nucleotide sequence having 95% or more identity with the nucleotide sequence set forth in SEQ ID NO: 2, and encoding a protein having alcohol oxidase activity.

* * * * *

SEQUENCE LISTING

<160> NUMBER OF SEQ ID NOS: 17

<210> SEQ ID NO 1
<211> LENGTH: 681
<212> TYPE: PRT
<213> ORGANISM: Candida bombicola NBRC10243

<400> SEQUENCE: 1

```
Met Thr Asp Ala Val Ile Leu Tyr Asp Tyr Glu Trp Gln Thr Leu Arg
1               5                   10                  15

Ala Leu Ala Asn Thr Ala Phe Pro Pro Leu His Ala Asp Gly Leu Leu
            20                  25                  30

His Gln Arg Ala Cys Glu Arg Val Ile Ser Met Leu Tyr Thr Gly Gln
        35                  40                  45

Lys Arg Ala Leu Arg Leu Met Leu His Ala Leu Ser Phe Arg Gly Ser
    50                  55                  60

Ala Val Gly Phe Thr Arg Ser Tyr Lys Leu Val Thr Glu Met Thr Glu
65                  70                  75                  80

Glu Glu Val Gln Gln Val Phe Leu Gly Phe Val His Ser Arg Ile Gly
                85                  90                  95
```

```
Ser Leu Arg Met Phe Ala Thr Gly Ile Thr Ser Leu Ala Leu Leu Val
            100                 105                 110

Ala Tyr Arg Val Ser Pro Glu Leu Arg Lys Thr Leu Gly Asp Ala Asp
        115                 120                 125

Thr His Pro His Leu Leu Ser Ile Lys Ala Lys Ile Asn Thr Lys Glu
    130                 135                 140

Val Ile Trp His Leu Pro Lys Phe Ala Ile Pro Pro Leu Ser Pro
145                 150                 155                 160

Asn Gln Pro Ala Ala Ile Thr Thr Asp Val Val Ile Val Gly Ser Gly
                165                 170                 175

Cys Ser Ser Met Val Ala Ser Tyr Leu Leu Thr Lys Lys Gly Phe Asn
            180                 185                 190

Val Ile Ile Val Glu Lys Gly Tyr His Ile Asn Ala Ile Thr Ser Pro
        195                 200                 205

Glu His Asp Phe Gln Arg Asp Ile Glu Ala Phe Gly Glu His Asn
    210                 215                 220

Met Thr Ser Ala Asp Ala Ser Thr Ile Val Val Ala Gly Ala Thr Val
225                 230                 235                 240

Gly Gly Gly Gly Ala Val Asn Trp Ser Cys Ser Leu Arg Pro Thr Glu
                245                 250                 255

Leu Val Arg Arg Glu Phe Val Gln Lys Gly Ala Pro Leu Tyr Gly Ser
            260                 265                 270

Lys Glu Phe Asp His Ala Leu Ala Glu Val Arg Val Met Gln Val
        275                 280                 285

Ser Thr Lys Phe Gly Leu Glu Gly Gly Ser Asp Asn Glu His Ser Phe
    290                 295                 300

Thr Asn Asp Leu Ile Leu Lys Ala Ser Glu Lys Leu Asn Tyr Arg Ala
305                 310                 315                 320

Lys Val Ala Gly Gln Asn Thr Gly Lys His Arg Ala Asn Ser Gly Phe
                325                 330                 335

Val Glu Phe Gly Ser Arg Gln Gly Glu Ala Glu Gly Val Ala Glu
            340                 345                 350

Trp Phe Arg Asn Ser Phe Asn Asn Gly Ala Arg Leu Leu Gln Arg Gly
        355                 360                 365

His Val Val Asn Ile Arg His His Asn Gly Tyr Ala Ser Gly Val Glu
    370                 375                 380

Val Val Val Asp Gly Ser Lys Thr Ile Leu Ile Asn Cys Lys Arg Val
385                 390                 395                 400

Val Cys Ala Ala Gly Ser Leu Gln Thr Pro Val Leu Leu Gln Arg Ser
                405                 410                 415

Gly Phe Lys Asn Ser His Ile Gly Lys Gly Leu Lys Leu His Pro Val
            420                 425                 430

Thr Ala Ala Tyr Gly Val Phe Pro Glu Gln Ile Val Asn Lys Arg Leu
        435                 440                 445

Asp Pro Ile Met Thr Thr Val Cys Thr Glu Val Asp Asn Leu Asp Gly
    450                 455                 460

Glu Gly His Gly Pro Lys Ile Glu Ala Leu His His Arg Pro Leu Leu
465                 470                 475                 480

Thr Ser Phe Pro Leu Pro Tyr Arg Asp Ala Lys Asp Phe Gln Thr Lys
                485                 490                 495

Val Glu Ser Trp Glu His Leu Cys Thr Leu Leu Val Ile Thr Arg Asp
            500                 505                 510
```

| | | | | | | | | | | | | |
|---|---|---|---|---|---|---|---|---|---|---|---|---|
| Lys | Gly | Glu | Gly | Lys | Val | Ser | Phe | Tyr | Pro | Pro | Asn | Pro | Ser | Lys | Pro |
| | | | 515 | | | | | 520 | | | | | 525 | | |
| Tyr | Ile | Glu | Tyr | Thr | Pro | Ser | Lys | Tyr | Asp | Leu | Gly | Ala | Leu | Leu | Lys |
| | 530 | | | | | 535 | | | | | 540 | | | | |
| Gly | Ser | Leu | Ser | Ala | Ala | Asn | Met | Leu | Tyr | Val | Gln | Gly | Ala | Gln | Arg |
| 545 | | | | | 550 | | | | | 555 | | | | | 560 |
| Ile | Phe | Leu | Ser | Ser | Thr | Phe | Ile | Pro | Asp | Phe | Val | Ser | Asn | Lys | Pro |
| | | | | 565 | | | | | 570 | | | | | 575 | |
| Val | Ser | Glu | Arg | Ser | Ile | Trp | Asp | Asp | Tyr | Gln | Lys | Trp | Tyr | Gln |
| | | | 580 | | | | | 585 | | | | | 590 | |
| Glu | Ala | Lys | Arg | Lys | Glu | Phe | Ile | Leu | Tyr | Asp | Thr | Lys | Val | Gly | Ser |
| | | 595 | | | | | 600 | | | | | 605 | | | |
| Ala | His | Gln | Met | Gly | Thr | Cys | Arg | Met | Ser | Val | Asn | Gly | Pro | Lys | His |
| | 610 | | | | | 615 | | | | | 620 | | | | |
| Gly | Ala | Val | Asp | Gly | Lys | Gly | His | Leu | Tyr | Glu | Cys | Pro | Asn | Val | His |
| 625 | | | | | 630 | | | | | 635 | | | | | 640 |
| Val | Ile | Asp | Thr | Ser | Val | Phe | Pro | Ala | Ala | Ser | Gly | Val | Asn | Pro | Met |
| | | | | 645 | | | | | 650 | | | | | 655 | |
| Ile | Thr | Cys | Met | Ala | Thr | Ala | Tyr | Val | Leu | Ala | Asn | Asn | Leu | Ile | Ala |
| | | | 660 | | | | | 665 | | | | | 670 | | |
| Asp | Leu | Thr | Lys | Leu | Gln | Thr | Lys | Leu |
| | | | 675 | | | | | 680 |

<210> SEQ ID NO 2
<211> LENGTH: 2046
<212> TYPE: DNA
<213> ORGANISM: Candida bombicola NBRC10243

<400> SEQUENCE: 2

```
atgactgacg cagttatcct ctacgactac gagtggcaga ctctccgggc tctcgcgaat    60
actgcgtttc cgcctctaca tgcagatggc ttgctccacc aaagagcctg tgagcgggtt   120
atttcgatgc tctacactgg ccaaaagcgg gcacttcggc ttatgctgca cgcccttagc   180
ttcagaggtt ctgccgtggg cttcaccagg tcttataagc ttgtgactga tgacggaa     240
gaggaggtcc aacaggtatt tcttggtttt gtgcattctc gcattggttc cttgagaatg   300
tttgccacag gaatcaccag ccttgctctt tagttgcct  acagagtgtc cccggagttg   360
cgcaagactc tcggggatgc tgacacgcac cctcatcttc ttagtatcaa ggcaaaaatc   420
aatacaaaag aggttatttg gcatctgccc aaattcgcaa tcccccctcc tctaagtcca   480
aatcagcctg cagcgataac cacggatgtt gtgattgttg gttccggttg ctcaagtatg   540
gtggcttctt atcttttgac aaagaagggt tcaatgtga  tcattgtgga aaaaggctac   600
cacatcaatg caattaccag tcccgaacac gacttccaac gtgacatcga ggcgtttgag   660
ggtgaacaca atatgacatc tgcggatgcc tcaacaatag ttgttgcggg cgccacggtc   720
ggaggcggtg gtgcagttaa ctggagctgt tccttacgtc caactgagct tgttagacgt   780
gagtttgtcc agaaaggagc tccactctat ggctcgaaag agtttgacca cgctttggct   840
gaggtcgaac gggttatgca gtaagcact  aagttcggtc ttgagggtgg cagcgataac   900
gaacattcat tcacgaacga tttgatcttg aaggccagcg agaagctcaa ttatcgagcc   960
aaggtcgcag gtcaaaatac tgggaagcac agagcaaact ctggcttcgt cgagtttggc  1020
agcagacagg gcgaggctga aggcggggtc gctgagtggt ccgcaacag  tttcaacaac  1080
ggtgctcggt tgctgcagag aggccacgtt gtcaacatca ggcaccataa cggttacgcc  1140
```

```
tctggtgtag aggtagttgt agacgggtca agaccatttt tgataaactg caaacgagtt   1200
gtgtgcgctg cagggtcact tcagactcca gtgctgctgc agaggtcagg tttcaagaac   1260
tctcatatcg gcaagggcct gaaattgcac ccggtcactg cagcttatgg tgtcttcccc   1320
gaacagatag tgaacaagcg acttgatccc attatgacca cggtttgcac agaagtcgac   1380
aatctcgacg gtgaaggcca cgggccaaag atcgaggcgc tgcaccacag gcctcttctc   1440
acatccttcc ctctgccata ccgcgatgcc aaggactttc aaaccaaggt ggagagctgg   1500
gagcatcttt gcacgcttct ggtcatcact cgtgataagg gagaaggcaa agtgagcttt   1560 tatccccga atccctcaaa gccttatatc gaatacacgc cgagcaagta tgatcttggg   1620
gctctgctga aagggtccct gtctgctgcg aacatgcttt acgtacaagg cgcgcaacgc   1680
atattcttgt caagcacatt catccccgat ttcgtatcca ataagccggt atctgagcga   1740
tcaatttggg acgacgacta tcagaaatgg taccaggagg ccaagcgcaa ggaattcatt   1800
ctatatgaca ctaaagttgg gtctgctcat caaatgggta cctgtcgcat gagcgtgaac   1860
gggcccaagc atggcgccgt tgacggaaag ggacaccttt acgagtgccc caatgttcac   1920
gttattgata cttcggtgtt tcccgctgct tcgggcgtca atccgatgat aacgtgcatg   1980
gctactgctt acgtgcttgc aaacaatctt atcgcggatc tcactaagct tcaaactaag   2040
ctatga                                                              2046

<210> SEQ ID NO 3
<211> LENGTH: 35
<212> TYPE: DNA
<213> ORGANISM: Artificial Sequence
<220> FEATURE:
<223> OTHER INFORMATION: PCR primer AOX1 US in F1

<400> SEQUENCE: 3
agcttgcatg cctgctttaa atccagaaag aactg                               35

<210> SEQ ID NO 4
<211> LENGTH: 35
<212> TYPE: DNA
<213> ORGANISM: Artificial Sequence
<220> FEATURE:
<223> OTHER INFORMATION: PCR primer AOX1 US-ura R

<400> SEQUENCE: 4
cgaaaaatat gtactgataa ctgcgtcagt cattg                               35

<210> SEQ ID NO 5
<211> LENGTH: 28
<212> TYPE: DNA
<213> ORGANISM: Artificial Sequence
<220> FEATURE:
<223> OTHER INFORMATION: PCR primer Pura3 F

<400> SEQUENCE: 5
agtacatatt tttcgaaaca gctcgcaa                                       28

<210> SEQ ID NO 6
<211> LENGTH: 29
<212> TYPE: DNA
<213> ORGANISM: Artificial Sequence
<220> FEATURE:
<223> OTHER INFORMATION: PCR primer ura3 R

<400> SEQUENCE: 6
ctaagaaact catcttgact gaactttc                                       29
```

```
<210> SEQ ID NO 7
<211> LENGTH: 35
<212> TYPE: DNA
<213> ORGANISM: Artificial Sequence
<220> FEATURE:
<223> OTHER INFORMATION: PCR primer ura-AOX1 LS F

<400> SEQUENCE: 7
agatgagttt cttagaagcc ttatatcgaa tacac                              35

<210> SEQ ID NO 8
<211> LENGTH: 35
<212> TYPE: DNA
<213> ORGANISM: Artificial Sequence
<220> FEATURE:
<223> OTHER INFORMATION: PCR primer AOX1 LS in R1

<400> SEQUENCE: 8
attcgagctc ggtacgacac ttctcaggaa ccctc                              35

<210> SEQ ID NO 9
<211> LENGTH: 19
<212> TYPE: DNA
<213> ORGANISM: Artificial Sequence
<220> FEATURE:
<223> OTHER INFORMATION: PCR primer pUC in F2

<400> SEQUENCE: 9
gtaccgagct cgaattcgt                                                19

<210> SEQ ID NO 10
<211> LENGTH: 19
<212> TYPE: DNA
<213> ORGANISM: Artificial Sequence
<220> FEATURE:
<223> OTHER INFORMATION: PCR primer pUC in R2

<400> SEQUENCE: 10
gcaggcatgc aagcttggc                                                19

<210> SEQ ID NO 11
<211> LENGTH: 18
<212> TYPE: DNA
<213> ORGANISM: Artificial Sequence
<220> FEATURE:
<223> OTHER INFORMATION: PCR primer ura3 R2

<400> SEQUENCE: 11
ttcatcatcg tcactata                                                 18

<210> SEQ ID NO 12
<211> LENGTH: 18
<212> TYPE: DNA
<213> ORGANISM: Artificial Sequence
<220> FEATURE:
<223> OTHER INFORMATION: PCR primer pUC seq 1

<400> SEQUENCE: 12
ggcgaaaggg ggatgtgc                                                 18

<210> SEQ ID NO 13
<211> LENGTH: 18
<212> TYPE: DNA
<213> ORGANISM: Artificial Sequence
<220> FEATURE:
<223> OTHER INFORMATION: PCR primer pUC seq 2
```

```
<400> SEQUENCE: 13 gcacccccagg ctttacac                                               18

<210> SEQ ID NO 14
<211> LENGTH: 36
<212> TYPE: DNA
<213> ORGANISM: Artificial Sequence
<220> FEATURE:
<223> OTHER INFORMATION: PCR primer AOX F

<400> SEQUENCE: 14
gaaggagata tacatatgac tgacgcagtt atcctc                            36

<210> SEQ ID NO 15
<211> LENGTH: 35
<212> TYPE: DNA
<213> ORGANISM: Artificial Sequence
<220> FEATURE:
<223> OTHER INFORMATION: PCR primer AOX R

<400> SEQUENCE: 15
agtgcggccg caagctagct tagtttgaag cttag                             35

<210> SEQ ID NO 16
<211> LENGTH: 19
<212> TYPE: DNA
<213> ORGANISM: Artificial Sequence
<220> FEATURE:
<223> OTHER INFORMATION: PCR primer pET21 F

<400> SEQUENCE: 16
gcttgcggcc gcactcgag                                               19

<210> SEQ ID NO 17
<211> LENGTH: 21
<212> TYPE: DNA
<213> ORGANISM: Artificial Sequence
<220> FEATURE:
<223> OTHER INFORMATION: PCR primer pET21 R

<400> SEQUENCE: 17
atgtatatct ccttcttaaa g                                            21
```